(12) United States Patent
Beutter et al.

(10) Patent No.: US 8,246,661 B2
(45) Date of Patent: Aug. 21, 2012

(54) BONE PLATE

(75) Inventors: Florian Beutter, Solothurn (CH);
Andreas Appenzeller, Biel (CH);
Franco Cicoira, Selzach (CH); Robert Frigg, Bettlach (CH)

(73) Assignee: Synthes USA, LLC, West Chester, PA (US)

( * ) Notice: Subject to any disclaimer, the term of this patent is extended or adjusted under 35 U.S.C. 154(b) by 1512 days.

(21) Appl. No.: 11/416,489

(22) Filed: May 1, 2006

(65) Prior Publication Data
US 2007/0016205 A1    Jan. 18, 2007

Related U.S. Application Data

(63) Continuation of application No. PCT/CH03/00712, filed on Oct. 30, 2003.

(51) Int. Cl.
*A61F 2/30* (2006.01)
(52) U.S. Cl. ........................................ 606/280
(58) Field of Classification Search .............. 606/60, 606/61, 69, 70, 71, 72, 73, 246–279, 280–299, 606/300–331
See application file for complete search history.

(56) References Cited

U.S. PATENT DOCUMENTS

| | | | |
|---|---|---|---|
| 3,463,148 A | 8/1969 | Treace | |
| 3,552,389 A * | 1/1971 | Allgower et al. | 606/282 |
| 3,630,261 A | 12/1971 | Gley | |
| 3,668,972 A | 6/1972 | Allgower et al. | |
| 3,716,050 A * | 2/1973 | Johnston | 606/286 |
| 3,741,205 A | 6/1973 | Markolf et al. | |
| 3,779,240 A | 12/1973 | Kondo | |
| RE28,841 E | 6/1976 | Allgower et al. | |
| 4,029,091 A | 6/1977 | Von Bezold et al. | |
| 4,175,555 A | 11/1979 | Herbert | |

(Continued)

FOREIGN PATENT DOCUMENTS

CA    1112803    11/1981

(Continued)

OTHER PUBLICATIONS

ACE Symmetry™ Titanium Upper Extremity Plates, ACE Medical Company.

(Continued)

*Primary Examiner* — Eduardo C. Robert
*Assistant Examiner* — Christopher Beccia
(74) *Attorney, Agent, or Firm* — Fay Kaplun & Marcin, LLP

(57) ABSTRACT

A bone plate (1) having an upper side (2), a bone-sided lower side (3), a first end (11), a second end (12) and several plate holes (4) arranged between the two ends (11, 12) and connecting the upper side (2) to the lower side (3), the plate holes being provided for receiving bone screws. Two of the plate holes (4) are formed by a combination of two partially overlapping boreholes (5, 6) of different type. The first (5) of the two boreholes is a circular cylindrical bore, having an internal thread (7) and a cylinder axis (9). The second borehole (6) has a cone axis (10) and tapers from the upper side (2) to the lower side (3) in the form of a frustum of a cone. The second borehole (6) is provided with an internal thread (8). The cylinder axis (9) is situated at a distance A from the cone axis (10), where A is different than zero.

17 Claims, 1 Drawing Sheet

U.S. PATENT DOCUMENTS

| Patent No. | | Date | Inventor | Ref |
|---|---|---|---|---|
| 4,219,015 | A | 8/1980 | Steinemann | |
| 4,263,904 | A | 4/1981 | Judet | |
| 4,338,926 | A | 7/1982 | Kummer et al. | |
| 4,408,601 | A | 10/1983 | Wenk | |
| 4,429,690 | A | 2/1984 | Angelino-Pievani | |
| RE31,628 | E | 7/1984 | Allgower et al. | |
| 4,484,570 | A | 11/1984 | Sutter et al. | |
| 4,493,317 | A | 1/1985 | Klaue | |
| 4,513,744 | A | 4/1985 | Klaue | |
| 4,565,193 | A | 1/1986 | Streli | |
| 4,612,923 | A | 9/1986 | Kronenthal | |
| 4,651,724 | A | 3/1987 | Berentey et al. | |
| 4,683,878 | A * | 8/1987 | Carter | 606/97 |
| 4,776,329 | A | 10/1988 | Treharne | |
| 4,781,183 | A | 11/1988 | Casey et al. | |
| 4,838,252 | A | 6/1989 | Klaue | |
| 4,858,601 | A | 8/1989 | Glisson | |
| 4,867,144 | A | 9/1989 | Karas et al. | |
| 4,927,421 | A | 5/1990 | Goble et al. | |
| 4,957,497 | A | 9/1990 | Hoogland et al. | |
| 4,988,350 | A | 1/1991 | Herzberg | |
| 5,002,544 | A | 3/1991 | Klaue et al. | |
| 5,006,120 | A | 4/1991 | Carter | |
| 5,041,113 | A | 8/1991 | Biedermann et al. | |
| 5,041,114 | A | 8/1991 | Chapman et al. | |
| 5,053,036 | A | 10/1991 | Perren et al. | |
| 5,085,660 | A | 2/1992 | Lin | |
| 5,129,901 | A | 7/1992 | Decoste | |
| 5,151,103 | A | 9/1992 | Tepic et al. | |
| 5,190,544 | A | 3/1993 | Chapman et al. | |
| 5,197,966 | A | 3/1993 | Sommerkamp | |
| 5,269,784 | A | 12/1993 | Mast | |
| 5,275,601 | A | 1/1994 | Gogolewski et al. | |
| 5,304,180 | A | 4/1994 | Slocum | |
| 5,324,290 | A | 6/1994 | Zdeblick et al. | |
| 5,336,224 | A | 8/1994 | Selman | |
| 5,360,448 | A | 11/1994 | Thramann | |
| 5,364,398 | A | 11/1994 | Chapman et al. | |
| 5,364,399 | A | 11/1994 | Lowery et al. | |
| 5,429,641 | A | 7/1995 | Gotfried | |
| 5,514,138 | A | 5/1996 | McCarthy | |
| 5,591,168 | A | 1/1997 | Judet et al. | |
| 5,601,553 | A | 2/1997 | Trebing et al. | |
| 5,607,426 | A | 3/1997 | Ralph et al. | |
| 5,607,428 | A | 3/1997 | Lin | |
| 5,674,222 | A | 10/1997 | Berger et al. | |
| 5,702,399 | A | 12/1997 | Kilpela et al. | |
| 5,709,686 | A * | 1/1998 | Talos et al. | 606/281 |
| 5,741,258 | A | 4/1998 | Klaue et al. | |
| 5,749,872 | A | 5/1998 | Kyle et al. | |
| 5,772,662 | A | 6/1998 | Chapman et al. | |
| 5,810,823 | A | 9/1998 | Klaue et al. | |
| 5,938,664 | A | 8/1999 | Winquist et al. | |
| 5,954,722 | A | 9/1999 | Bono | |
| 5,968,047 | A | 10/1999 | Reed | |
| 5,976,141 | A | 11/1999 | Haag | |
| 6,022,352 | A | 2/2000 | Vandewalle | |
| 6,030,389 | A * | 2/2000 | Wagner et al. | 606/71 |
| 6,096,040 | A | 8/2000 | Esser | |
| 6,129,730 | A | 10/2000 | Bono et al. | |
| 6,183,475 | B1 | 2/2001 | Lester et al. | |
| 6,206,881 | B1 | 3/2001 | Frigg et al. | |
| 6,228,085 | B1 | 5/2001 | Theken et al. | |
| 6,306,136 | B1 | 10/2001 | Baccelli | |
| 6,322,562 | B1 | 11/2001 | Wolter | |
| 6,348,052 | B1 * | 2/2002 | Sammarco | 606/284 |
| 6,364,882 | B1 | 4/2002 | Orbay | |
| 6,423,064 | B1 | 7/2002 | Kluger | |
| 6,440,135 | B2 | 8/2002 | Orbay et al. | |
| 6,454,769 | B2 | 9/2002 | Wagner et al. | |
| 6,454,770 | B2 | 9/2002 | Klaue | |
| 6,527,776 | B1 | 3/2003 | Michelson | |
| 6,565,569 | B1 | 5/2003 | Assaker et al. | |
| 6,575,975 | B2 | 6/2003 | Brace et al. | |
| D479,331 | S | 9/2003 | Pike et al. | |
| 6,623,486 | B1 | 9/2003 | Weaver et al. | |
| 6,669,701 | B2 * | 12/2003 | Steiner et al. | 606/282 |
| 6,719,759 | B2 * | 4/2004 | Wagner et al. | 606/282 |
| 7,044,953 | B2 | 5/2006 | Capanni | |
| 7,128,744 | B2 * | 10/2006 | Weaver et al. | 606/280 |
| 7,229,445 | B2 * | 6/2007 | Hayeck et al. | 606/70 |
| 2002/0183752 | A1 * | 12/2002 | Steiner et al. | 606/69 |
| 2004/0073218 | A1 | 4/2004 | Dahners | |
| 2004/0167522 | A1 * | 8/2004 | Niederberger et al. | 606/69 |
| 2005/0165400 | A1 | 7/2005 | Fernandez | |
| 2006/0217722 | A1 | 9/2006 | Dutoit et al. | |
| 2006/0235400 | A1 | 10/2006 | Schneider | |

FOREIGN PATENT DOCUMENTS

| | | |
|---|---|---|
| CH | 611147 A5 | 5/1979 |
| DE | 34 42 004 C1 | 4/1986 |
| DE | 43 41 980 A1 | 6/1995 |
| DE | 43 43 117 A1 | 6/1995 |
| DE | 44 38 264 A1 | 3/1996 |
| DE | 93 21 544 U1 | 10/1999 |
| DE | 198 32 513 A1 | 2/2000 |
| DE | 203 09 361 U1 | 9/2003 |
| EP | 0 053 999 A1 | 6/1982 |
| EP | 0 207 884 A2 | 1/1987 |
| EP | 0 410 309 A1 | 1/1991 |
| EP | 0 515 828 A1 | 12/1992 |
| EP | 0 530 585 A2 | 3/1993 |
| EP | 1 468 655 A2 | 10/2004 |
| FR | 742 618 | 3/1933 |
| FR | 2 233 973 A1 | 2/1975 |
| FR | 2 405 062 A1 | 6/1979 |
| FR | 2 405 705 A1 | 6/1979 |
| FR | 2 405 706 A1 | 6/1979 |
| FR | 2 496 429 A3 | 6/1982 |
| FR | 2 674 118 A1 | 9/1992 |
| JP | 11299804 | 11/1992 |
| SU | 1 037 911 A | 8/1983 |
| SU | 1 279 626 A1 | 12/1986 |
| WO | WO 87/00419 A1 | 1/1987 |
| WO | WO 88/03781 A1 | 6/1988 |
| WO | WO 96/29948 A1 | 10/1996 |
| WO | WO 97/09000 A1 | 3/1997 |
| WO | WO 00/53110 A1 | 9/2000 |
| WO | WO 00/66012 A1 | 11/2000 |
| WO | WO 01/54601 A1 | 8/2001 |
| WO | WO 02/096309 A1 | 12/2002 |
| WO | WO 2004/089233 A1 | 10/2004 |

OTHER PUBLICATIONS

International Search Report for International Application No. PCT/CH03/00712. mailed Jun. 20, 2004, German language version.

International Search Report for International Application No. PCT/CH03/00712, mailed Jun. 30, 2004, English language translation of the German language version.

* cited by examiner

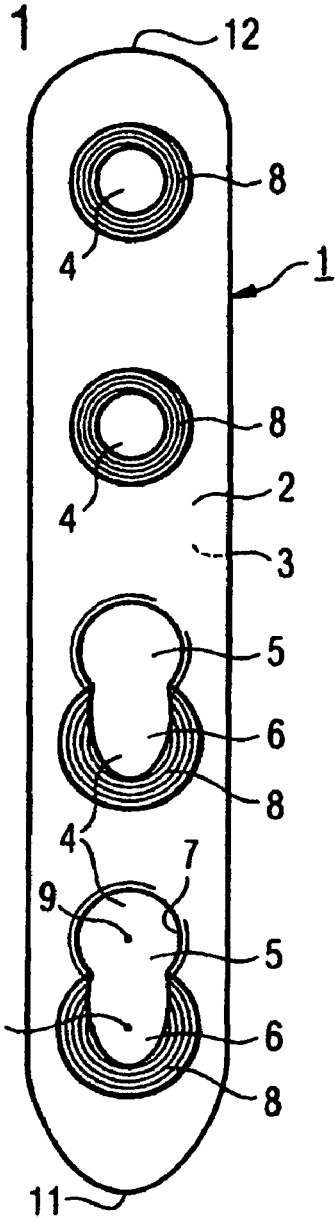
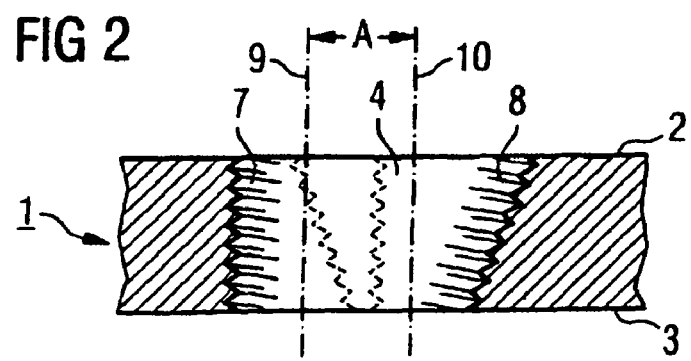

BONE PLATE

RELATED APPLICATION DATA

The present application is a continuation of the U.S. National Stage designation of co-pending International Patent Application No. PCT/CH2003/000712, filed Oct. 30, 2003, the entire content of which is expressly incorporated herein by reference thereto.

FIELD OF INVENTION

The present invention relates to a bone plate and, more particularly, to a bone plate having at least one combination hole formed by two different, partially overlapping through-holes.

BACKGROUND OF THE INVENTION

Primarily, the bone plate is intended to fix forefoot osteotomies, in particular hallux valgus osteotomies. Such osteotomies, or their fixations, should obey the following criteria:
they should be angularly fixed,
they should match the corresponding size of the correction,
they should be minimally invasive.

An implant in the form of a clamp is known from the patent documents WO 00/06036 and AT 000937U2 and is used intramedullarily. Said clamp offers the advantage of minimal invasiveness for intramedullary fixation; however, the implant per se is not angularly fixed. The correction depends on the various crimps by which the clamp is presented. Accordingly, the clamp is minimally invasive but cannot fix small corrections.

The FRIGG publication WO 01/54601 discloses a bone plate with combined holes, i.e., two mutually penetrating plate boreholes. This combined hole incurs the drawback that only one of the two plate boreholes includes a partial, internal thread, and that, consequently, an angularly fixed, rigid anchoring of a bone screw is possible only in that single plate borehole.

The objective of the present invention is palliation. The invention's goal is to create a bone plate which is applicable both intramedullarily and extramedullarily and which allows angular and minimally invasive fixation of both small and large corrections.

SUMMARY OF THE INVENTION

The invention attains its objective using a bone plate comprising an upper surface, a lower surface, first and second ends, and at least one combination hole disposed between the first and second ends, the hole passing through the upper and lower surfaces and configured and dimensioned for receiving at least one bone fastener. The combination hole may be formed by two different, partially overlapping bores, where the first bore has a cylindrical shape defining a central cylinder axis, and the second bore, which tapers from the upper surface to the lower surface, has a frusto-conical shape defining a central cone axis. The cylinder axis is spaced a non-zero distance from the cone axis. Preferably, both the cylindrical and frusto-conical bores include at least partial internal threads.

Said bone plate meets all the above listed requirements, namely:

(a) Being Angularly Fixed:

The bone plate is bilaterally adequately angularly fixed by means of two slots in the shank and two slots in the head zone of the metatarsal bone. Furthermore, on account of two cylindrical threads within the plate in the shank zone and by locking this plate using two screws, said plate is protected also against rotation as well as being shifted within the medullary cavity.

(b) Fixation According to the Size of the Correction:

This feature is implemented using the target bail. The small MT head shall be shifted to the desired extent in the lateral direction. Thereupon the plate is inserted or hammered in position along the small head and then is screwed tight.

(c) Minimal Invasiveness:

Sawing is carried out through an incision that is just wide enough to pass the saw blade. However said incision is large enough to insert the plate. The holes to screw in place the plate in the shank zone may be bored thereupon through the skin.

(d) Small Corrections also are Possible:

Small corrections not exceeding the cortical edge of the medullary space may be fixed extramedullarily using this plate. In this procedure the plate is slightly bent in relation to the correction and moved under the skin. The second part of the holes used to lock the shank are fitted with a conical thread and are intended for extramedullar, angular fixation. The holes may be felt when the plate is being moved under the skin. The incision between the two plates will then suffice to reach both holes.

Using the "combined hole" of the bone plate of the present invention, and, preferably, with two of such holes being configured in the lower, proximal bone plate part, said bone plate may be used both intramedullarily and extramedullarily.

The "combined hole" consists of a cylindrical and a conical portion each fitted with at least a partial thread. The cylindrical portion is used for intramedullar fixation and is locked by the shank thread of a bone screw. The conical portion is used for extramedullar bone plate application also to lock the bone plate, in this instance a socket head screw being used, resulting in a so-called "internal fixator." The small metatarsal head being the element being displaced, a selection in fixation (intramedullary, extramedullary) is not significant in this case. Therefore the two plate holes in the upper, distal zone of the bone plate correspond to the conventional, angularly fixed plate holes (circular cylindrical or conical inside thread holes).

A targeting element is required to fix the bone plate of the invention in an intramedullary manner and to allow accurate locking of the bone plate in the bone. Simultaneously, however, this targeting element may both enable precise placement of the bone plate and act as a hammer tool.

No targeting element is required for extramedullary fixation because the bone plate holes can be felt underneath the skin. The two "combined holes," preferably configured at the bone plate's proximal end, are so close to each other that they can be reached by using one incision and by displacing the skin.

The term "internal threads" denotes not only helical structures but also rib-shaped structures that may act as threads.

The bone plate of the present invention offers the advantage of entailing only little material waste when being manufactured. Another advantage is enabling a shorter bone plate, resulting in less invasiveness.

In a first preferred embodiment of the present invention, the plate hole consisting of two mutually overlapping boreholes is configured at the first bone plate end. In one embodiment, the first bone plate end tapers. As a result, the bone cavity will be more easily accessed and, as regards the extramedullary case, the bone plate will be more easily moved underneath the skin.

In another preferred embodiment, the internal thread of the first borehole is multiple, e.g., a double thread. This feature provides faster seizing when turning a socket head screw. The internal thread of the second borehole also may be multiple, preferably double.

In still another preferred embodiment, the cylinder axis and the cone axis of the two overlapping boreholes run essentially parallel to each other. The distance A between the axes of the cylinder and cone preferably shall be larger than 0.1 mm.

In yet another preferred embodiment, the bone plate comprises at least two boreholes formed by a combination of two different and partly overlapping boreholes. Preferably, an additional separate borehole adds to the first two boreholes but does not itself consist of two partly overlapping boreholes. The separate plate holes may be cylindrical or conical, with or without inside threads.

The bone plate comprises a compression hole in yet another embodiment of the present invention.

In still another embodiment, the second bone plate end is Y-shaped. On occasion, the fragment to be fixed will be too short to allow fixation with two consecutively located holes. In such a case, a Y-shaped bone plate end offers the advantage that each arm of the Y comprises one hole.

Preferably, one or even both of the two arms of the Y-shaped end includes a compression hole. A combined hole also may be used, that is, a combination of a compression hole and a locking hole. Again only one of the two kinds of holes (compression or locking hole) may be used.

A compression hole combined with a locking hole at the other Y arm offers the advantage that bone plate compression may take place before the second hole is used for angular fixation.

In still a further embodiment of the present invention, the upper and lower surfaces of the bone plate are curved. Typically the curved upper and lower sides correspond to the surfaces of circular cylinders $C_{upper}$ and $C_{lower}$.

Preferably the upper side (2) and the lower side (3) exhibit different curvatures. If the bone plate is used intramedullarily as well as extramedullarily, the different curvatures of top and bottom sides allow optimally matching the intramedullar surface of the medullary space on one hand and on the other hand the bone extramedullar surface.

In one particular embodiment, the radius $R_{upper}$ of the circular cylinder $C_{upper}$ is at most 50%, preferably at most 40%, of the radius $R_{lower}$ of the circular cylinder $C_{lower}$.

BRIEF DESCRIPTION OF THE DRAWINGS

The invention and its further developments are described below in relation to the partly schematic figures of several illustrative embodiments, in which:

FIG. 1 is a top view of a preferred embodiment of the bone plate of the invention having two "combined holes"; and FIG. 2 is a longitudinal section of the bone plate of FIG. 1 in the area of one of the combined holes.

DETAILED DESCRIPTION OF THE PREFERRED EMBODIMENTS

The bone plate 1 shown in FIGS. 1 and 2 comprises a top side 2, a bottom side 3 facing the bone, a first end 11, a second end 12 and four plate holes which shall receive the bone screws and which are configured between the two ends 11, 12 and connect the top side 2 to the bottom side 3.

The two plate holes 4 near the first end 11 are constituted by two different and partly overlapping boreholes 5, 6. The first (5) of the two boreholes is circular cylindrical and comprises a cylinder axis 9 and an inside thread 7. The second (6) of the two boreholes tapers from the top side 2 toward the bottom side 3 to subtend a cone frustrum and it comprises a conical axis 10 and an inside thread 8. The cylinder axis 9 and the cone axis 10 run parallel to each other and are a distance A=2 mm apart.

Of the two plate holes 4 constituted by the overlapping boreholes 5, 6, the terminal one is configured near the first and tapering end 11 of the bone plate 1.

The plate holes 4 adjoining the combined holes are conical, angularly fixed and comprise an inside thread 8.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed:

1. A bone plate comprising:
    an upper surface;
    a lower surface;
    first and second ends; and
    at least one combination hole disposed between the first and second ends, the hole passing through the upper and lower surfaces and configured and dimensioned for receiving at least one bone fastener,
    wherein the at least one combination hole is formed by two different, partially overlapping bores, the first bore having at least a partial first internal thread and a partially cylindrical portion defining a central cylinder axis, the partially cylindrical portion extending from the upper surface to the lower surface, the second bore tapering from the upper surface to the lower surface and having at least a partial second internal thread, the second bore including a partially frusto-conical portion defining a central cone axis, the cylinder axis spaced a non-zero distance from the cone axis.

2. The bone plate of claim 1, wherein the combination hole is located nearer the first end of the bone plate than the second end.

3. The bone plate of claim 1, wherein the first end of the bone plate is tapered.

4. The bone plate of claim 1, wherein the first bore includes multiple lead threads.

5. The bone plate of claim 1, wherein the second bore includes multiple lead threads.

6. The bone plate of claim 1, wherein the cylinder axis and the cone axis are substantially parallel.

7. The bone plate of claim 1, wherein the distance between the cylinder axis and the cone axis is greater than 0.1 mm.

8. The bone plate of claim 1, further comprising at least two combination holes.

9. The bone plate of claim 1, further including an additional hole wherein the additional hole is a non-threaded compression hole.

10. The bone plate of claim 1, wherein the second end of the plate is Y-shaped.

11. The bone plate of claim 10, wherein the second, Y-shaped end of the plate includes two aims, and at least one of the arms includes a non-threaded compression hole.

12. The bone plate of claim 1, wherein the upper and lower surfaces are curved.

13. The bone plate of claim 12, wherein the curved upper and lower surfaces are each partially cylindrically-shaped.

14. The bone plate of claim 13 wherein the curvature of the upper surface is different than the curvature of the lower surface.

15. The bone plate of claim 14 wherein the partially cylindrically-shaped upper surface has a first cylinder radius $R_{upper}$ and the partially cylindrically-shaped lower surface has a second cylinder radius $R_{lower}$, where $R_{upper}$ is less than or equal to 50% of $R_{lower}$.

16. The bone plate of claim 15, wherein $R_{upper}$ is less than or equal to 40% of $R_{lower}$.

17. A bone plate comprising:
    an upper surface;
    a lower surface;
    first and second ends;
    a first cylindrical bore disposed between the first and second ends including a partially cylindrical portion and having at least a partial first internal thread on the partially cylindrical portion, the cylindrical bore passing through the upper and lower surfaces and defining a central cylinder axis;
    a second frusto-conical bore disposed between the first and second ends including a partially conical portion and having at least a partial second internal thread on the partially conical portion, the frusto-conical bore passing through the upper and lower surfaces, forming a larger opening in the upper surface than the lower surface, and defining a central cone axis,
    wherein the first and second bores partially overlap one another to form a combination hole such that the cylinder axis is spaced a non-zero distance from the cone axis, the partially cylindrical portion of the first bore extending from the upper surface to the lower surface.

* * * * *